United States Patent [19]

Colling

[11] Patent Number: 5,143,243
[45] Date of Patent: Sep. 1, 1992

[54] PROTECTIVE BARRIER APPARATUS
[75] Inventor: Keith J. Colling, Brownsburg, Ind.
[73] Assignee: Inland Container Corporation, Indianapolis, Ind.
[21] Appl. No.: 693,382
[22] Filed: Apr. 30, 1991
[51] Int. Cl.⁵ .......................................... B65D 90/04
[52] U.S. Cl. .................... 220/409; 206/366; 206/370; 150/154
[58] Field of Search .............. 206/366, 370; 150/154, 150/158, 159, 165; 229/117.14; 220/94 R, 402, 409, 908, DIG. 21; 217/3 CV

[56] References Cited

U.S. PATENT DOCUMENTS

| | | | |
|---|---|---|---|
| 3,237,552 | 5/1964 | Cronheim | 220/94 R |
| 3,349,992 | 10/1967 | Skinner | 150/154 |
| 3,662,803 | 5/1972 | Kuvik | 150/154 |
| 3,949,897 | 4/1976 | Shaw et al. | 220/94 R |
| 4,178,977 | 12/1979 | Sur et al. | 150/154 |
| 4,628,007 | 12/1986 | Ledsham | 220/908 |
| 4,749,011 | 6/1988 | Rylander | 220/402 |
| 4,891,918 | 1/1990 | Wiley | 150/154 |
| 4,981,254 | 1/1991 | Depper | 229/117.14 |
| 5,049,024 | 9/1991 | Chien | 220/908 |
| 5,057,656 | 10/1991 | Galber | 206/366 |

FOREIGN PATENT DOCUMENTS

| | | | |
|---|---|---|---|
| 1083538 | 8/1980 | Canada | 150/154 |
| 157027 | 9/1939 | Fed. Rep. of Germany | 150/154 |
| 807400 | 1/1959 | United Kingdom | 150/154 |

Primary Examiner—David T. Fidei
Attorney, Agent, or Firm—Fitch, Even, Tabin & Flannery

[57] ABSTRACT

Disclosed is a protective carrying apparatus of puncture-resistant material sides which mates with medical waste containers. The apparatus acts as a barrier between the person handling the medical waste container and contaminated sharp objects which may protrude through the container. The apparatus may be readily employed in hospital and health care waste handling programs to provide a prophylactic protection against the transmission of infection or injury due to contaminated sharp objects which may be inside medical waste containers.

9 Claims, 2 Drawing Sheets

PROTECTIVE BARRIER APPARATUS

BACKGROUND OF THE INVENTION

1. Field of the Invention

The present invention pertains to procedures for handling and transporting medical waste having needles or other sharp objects capable of puncturing an attendant's skin, or otherwise producing injury or illness. More particularly, the present invention pertains to a barrier apparatus for protectively isolating a medical waste container while the container is transported by an attendant.

2. Description of the Related Art

Certain medical waste (i.e. needles and other sharp objects referred to in the industry as "sharps") have been associated with the transmission of infection or injury through puncture or cut wounds. Moreover, the fear of acquired immuno-deficiency syndrome has drawn national attention to medical waste handling practices. Hospitals in the United States generate about 800 million pounds of waste each year, about 15% of which is considered to be infectious waste by the EPA's definition. Other sources of infectious waste include physicians offices, dentists offices, outpatient clinics, nursing homes, ambulatory surgery centers, dialysis centers and blood banks.

The procedures for disposing of contaminated needles and other sharps capable of producing injury or illness include the use of rigid puncture-proof containers, cardboard containers, needle clippers or a combination of these. Nearly all hospitals have a written infectious waste management policy, and nearly all waste handlers receive formal training in proper handling procedures, including the potential health and safety hazards. Typical handling procedures include the use of proper barrier clothing such as gowns and puncture-resistant rubber gloves. Employees are typically warned to hold waste containers away from their body to avoid injury from protruding sharps. Often employees accidentally disregard these procedures by wearing inappropriate clothing or more typically, in the case of needle-stick injuries, by neglecting to hold containers away from their body. Since some medical waste containers can be rather large and cumbersome to carry, it is understandable how a waste handler would come to press the container against his body.

There are considerable costs associated with the manufacture of medical waste containers. Moreover, there are significant costs in developing and promulgating appropriate waste handling procedures. To control these costs, hospitals typically separate regular medical waste from infectious waste. Medical waste is typically placed in conventional cardboard containers, while infectious waste, including discarded needles and syringes, are placed in specially marked containers which warn of the hazardous nature of the content. However, employees must still exercise caution when handling regular medical waste containers because infectious sharps may accidently be placed into these containers. This creates a hazard to employees who handle cardboard medical waste containers. So, while a cost savings may be realized by separating medical waste from infectious waste and using lightweight, less expensive cardboard containers for medical waste, a potential hazard still exists.

Needle clippers provide a way to control the cost of medical waste containers while protecting employees from infection due to protruding sharps. It was popular to use needle clippers in the early 1980s, but these devices are no longer widely used because many professional organizations and agencies have recommended that clipping or cutting of needles not be practiced. The reasons for recommending against clipping include the potential for aerosolization of microorganisms during the clipping process, and the clipping process itself being an unnecessary, extra operation that could result in needle stick injuries.

Since the hazards associated with contaminated sharps being carried in medical waste containers remain common, it would be desirable to provide a cost-effective way to transport medical waste without increasing the cost of the containers or the cost of waste handling procedures.

SUMMARY OF THE INVENTION

It is an object according to the present invention to provide a barrier apparatus for protectively isolating an infectious waste container while the container is in transport.

Another object according to the present invention is to provide a reusable barrier apparatus to facilitate the use of cost-effective waste containers without compromising the safety of waste handlers, thereby providing a cost-effective solution to the problems associated with handling medical waste.

Another object of the present invention is to provide a barrier apparatus having hand holes which mate with the hand holes on the container, providing access thereto while avoiding compromising protection to a user's body.

Another object of the present invention is to provide a barrier apparatus having support means attached to the bottom of its walls to align and support the container.

These and other objects according to the present invention, which will become apparent from studying the appended description and drawings, are provided in a protective barrier apparatus for protectively isolating a medical waste container having a top wall and a side wall joined together at an outside corner of the container, the apparatus comprising:

a side panel for isolating the side wall of the container;

a top panel joined to the side panel and extending at an angle therefrom, for isolating the top wall of the container;

handle means joined to one of the top panel and side panels for lifting the apparatus into place on the container; and anchor means carried on one of the top panel and side panels for releasably securing the apparatus to the container to prevent inadvertent dislodgment therefrom.

BRIEF DESCRIPTION OF THE DRAWINGS

In the drawings, wherein like elements are referenced alike.

DETAILED DESCRIPTION OF THE PREFERRED EMBODIMENT

Figure 1:
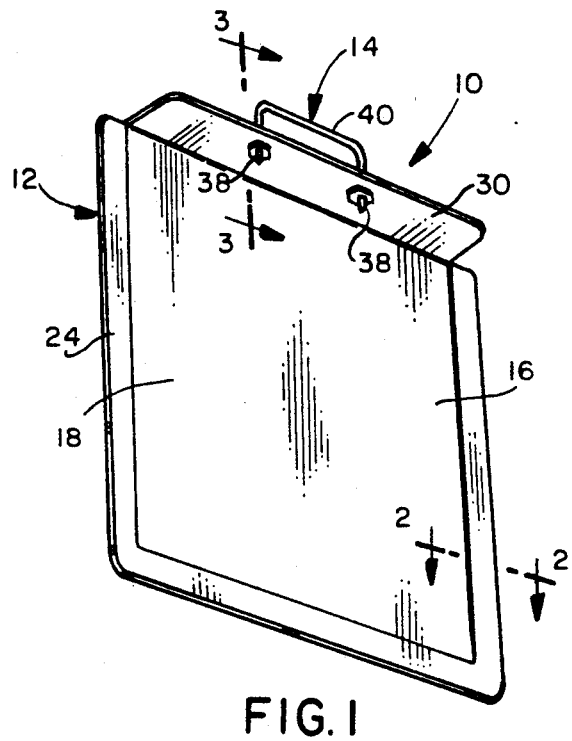
FIG. 1 is a perspective view of protective barrier apparatus according to principles of the present invention for protectively isolating an infectious waste container from operating personnel, especially while carrying the container.
Figure 2:
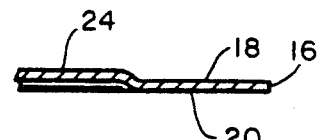
FIGS. 2 and 3 are fragmentary cross-sectional views taken along the lines 2—2 and 3—3, respectively of FIG. 1.
Figure 3:
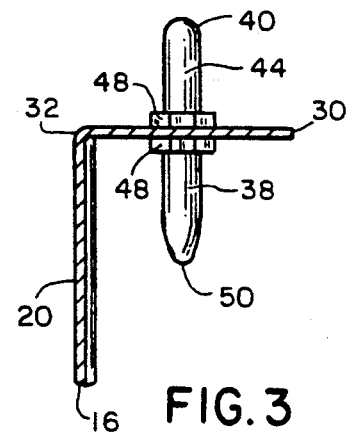

Referring now to the drawings, and initially to FIG. 1, protective barrier apparatus according to principles of the present invention is generally indicated at 10. In its preferred embodiment, the protective apparatus is constructed from two components, a shield member 12 and a handle assembly 14. The shield 12 is preferably formed from a single piece of relatively rigid, puncture-resistant material such as sheet metal or a suitably tough plastic such as nylon.

Figure 6:
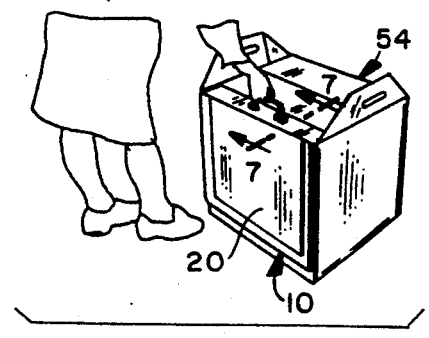
FIG. 6 is a perspective view showing the isolating barrier applied to a carton.
Figure 8:
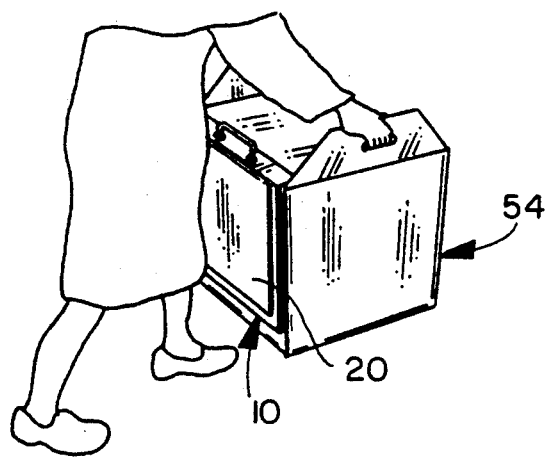
FIG. 8 is a perspective view showing the protective barrier in use.

Shield 12 includes a major panel 16 having an interior surface 18 (visible in FIG. 1) and an exterior surface 20 (visible in FIGS. 6 and 8). A border 24 surrounds the sides and bottom periphery of panel 16 and is recessed relative to the outer surface 20, thereby producing a concave structure when viewed from the interior, as illustrated in FIG. 1. Border 24, offset from the plane of panel 16, provides a strengthening for the panel preventing warping or other misalignment thereof and, by protruding outwardly away from interior surface 18 and insures a secure, intimate engagement with the sidewall of a carton to which the barrier apparatus is applied.

Shield 12 further includes an offset portion 30, preferably comprising a top horizontal panel which overlays the top of a carton. The offset portion 30 is offset from the plane of panel 16, to provide an added measure of protection at the upper corner of the carton and to provide an overhang over the carton top, thus allowing the anchoring pins to be positioned at interior portions of the carton top. In the preferred embodiment, the offset portion 30 is connected to panel 16 at a fold line or outside corner 32, a convenient construction for sheet metal and plastic materials, but the joinder may take on other conventional forms. In the preferred embodiment, the anchor pins 38 have tips 50, which are pointed with a round nose point. In the preferred embodiment, the shield 12 is made from sheet metal and the handle 40 is made from round wire stock and is secured to offset panel 30 of the shield with threaded nut fasteners 48.

In the preferred embodiment of the protective apparatus, the handle assembly 14 is conveniently made to include a pair of anchor means or pins 38 which, as will be seen herein, engage the carton preventing the shield from inadvertently dislodging from the carton, once applied thereto. The handle means 14 is preferably made from round wire stock and includes a U-shaped handle portion 40 extending above the offset panel 30 and having side legs 44, providing a standoff for the handle portion above panel 30. According to one aspect of the present invention, the side legs 44 extend significant distances below panel 30, to thereby comprise a convenient anchoring means for the protective apparatus, the lower portions of side legs comprising anchor pins 38.

Figure 4:
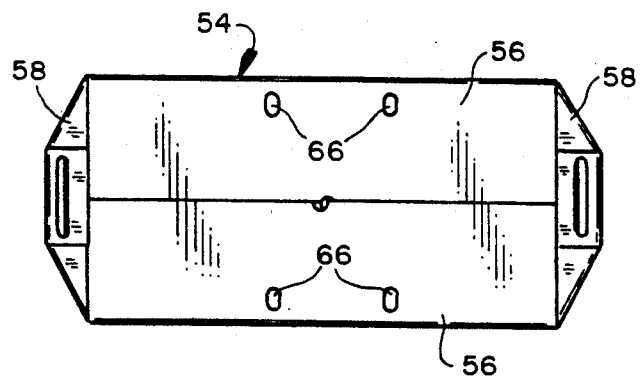
FIG. 4 is a top plan view of a carton through which the protective barrier is to be applied.
Figure 7:
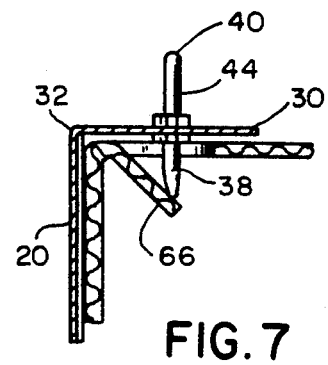
FIG. 7 is a fragmentary cross-sectional view taken along the line 7—7 of FIG. 6.
Figure 5:
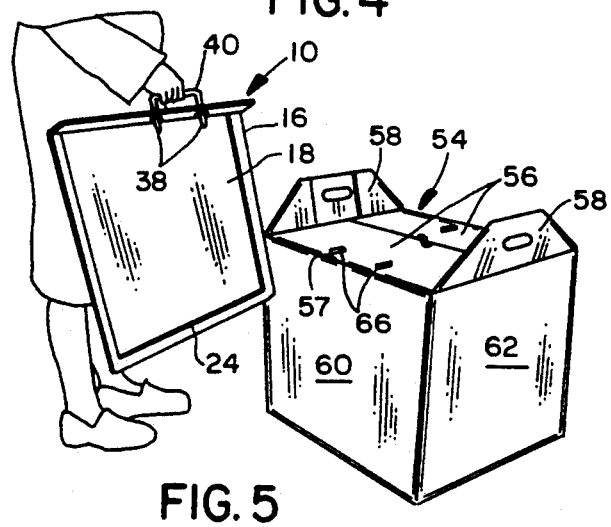
FIG. 5 is a perspective view showing a protective barrier about to be applied to a carton.

FIG. 4 illustrates one type of device to which the barrier apparatus may be applied. A corrugated paperboard carton is generally indicated at 54. Carton 54 includes top panels 56 and upstanding lug-type handles 58 protruding thereabove. Referring additionally to FIG. 5, carton 54 further includes side panels 60 and end panels 62, along with knockout tabs 66 which are partially cut out from top panels 56 so as to leave a connection to the top panels along hinge lines. The side panel 60, for example, is joined to top panel 56 at an outside corner 57 of the carton (see FIG. 5).

Referring now to FIGS. 5–8, operation of the protective apparatus will be described. As illustrated in FIG. 5, the protective apparatus is lifted by grasping handle portion 40 so as to position the panel 16 between the carton and the operator. Next, the shield is advanced toward sidewall 60 of the carton with the flange 24 contacting the carton sidewall. The protective apparatus is then lowered onto carton 54, with the flange 24 providing a convenient alignment and protection during lowering. The protective apparatus is then lowered, with offset panel 30 shielding an operator's hands from the carton 54 as the anchor pins 38 are lowered into contact with the tabs 66, deflecting the tabs inwardly in the manner indicated in FIG. 7. Preferably, the offset panel 30 has a width generally corresponding to the width of the carton, to afford a ready visual alignment for centering the protective apparatus on the carton, thereby aligning the anchor pins with the tabs 66. As will now be appreciated, the operator's hands and the remainder of the operator's person are continuously shielded from carton 54 during installation of the protective apparatus.

By completing the steps outlined above, the protective apparatus is installed, being secured against inadvertent dislodgment. As will now be appreciated, the protective apparatus must be lifted in a generally vertical direction to disengage the protective apparatus from the carton. Such alignment is relatively easy when the carton is resting on a support surface, but is relatively difficult when the carton is being carried or lifted, thereby adding to the security of the protective device. Further, the protective device remains securely fastened to the carton in position to protect service personnel transporting the carton, for example. For instance, it is important when carrying the carton that the service personnel be able to focus their attention on objects and other people who may be present in the area and to negotiate stairs and corners with a high degree of safety. It is important therefore, that the service personnel are not distracted from such matters of importance by a need to spend an inordinate amount of attention on the protective apparatus. As mentioned above, the protective apparatus in its preferred form is fabricated from sheet metal stock. Due to the relatively large size of the major panel, the vertical orientation of the major panel and the relatively small size of the offset panel, the protective apparatus experiences a force substantially oriented in a downward direction, which effectively maintains a secure engagement of the protective apparatus to the carton and which easily overcomes any forces tending to dislodge the protective apparatus, such as jostling of the carton during lifting or walking.

The carton 54 used to illustrate the features of the protective apparatus has lug-type handles upstanding above the top panel of the carton. It should be understood, however, that protective apparatus according to the present invention can be readily employed with cartons of other configurations, especially cartons which do not have upstanding handles, and can also be used with devices other than cartons such as trays, open top waste receptacles and conventional two-wheel dollies. For example, conventional two-wheel dollies have an open framework back against which cartons or other various objects come to rest when the dolly is inclined for transport. A protective shield according to the present invention can easily hook onto lateral members of the open work back and thus provide substantial protection to service personnel without modifying existing equipment. Further, it is common practice to stack cartons one on top of another and to transport the stack using a two-wheel dolly or similar device. The protective apparatus according to the present invention can remain affixed to each carton in the stack during such moving operations, thereby obviating the need for a shield on the dolly, or modifying the dolly for a special purpose.

Figure 9:
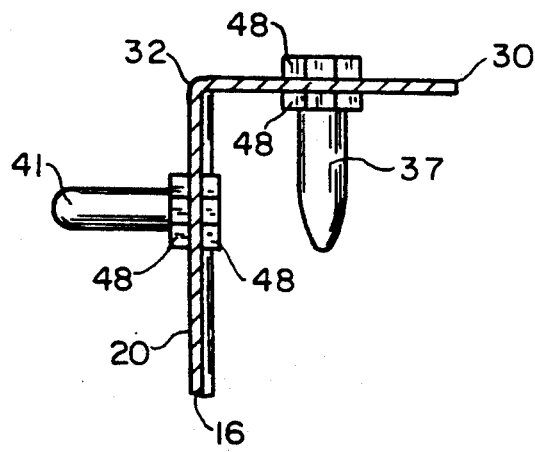
FIG. 9 is a fragmentary cross-section view showing an alternative embodiment of protective barrier apparatus according to principles of the present invention.
Figure 10:
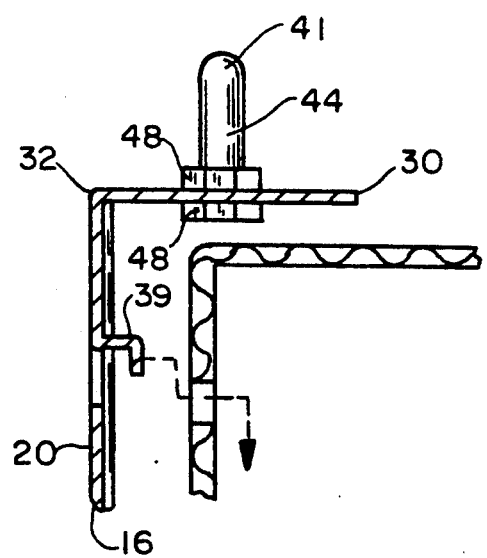
FIG. 10 is an exploded fragmentary perspective view showing another alternative embodiment of protective barrier apparatus according to principles of the present invention.

Additional changes and variations in the above are also contemplated by the present invention. For example, the handle and anchor pins are preferably formed from an integral wire stock. However, the anchor pins could be formed separately from the handle and could be formed from a separate member, such as a smaller piece of stamped metal welded or otherwise bonded to panels of the protective apparatus (see pin 37 in FIG. 9). Further, the handle has been described as being applied to the top or offset panel, although it could also be mounted to the side panel (see handle 41 in FIG. 9). The anchor pins have been described as extending from the top, offset panel, although they too could extend from the side panel and could be embodied in, for example, a plurality of dogleg shaped tabs 39 which are inserted into sidewalls of the carton in a direction generally perpendicular thereto, and thereafter shifted downwardly into a locked position (see FIG. 10).

In addition to the protective barrier, the carton described and illustrated above having partially formed tabs in a top panel thereof, adjacent a sidewall to be shielded, is believed to be novel. The tabs are formed by cut or perforation lines, except for one side of the tab which forms a fold or hinge line. Joinder of the remaining portion of the tabs to the top wall is weakened by the cut or perforation lines so that the tabs are readily deflected by a suitably blunt instrument, small enough to rest solely on the tabs, but much less pointed than the sharps which may be contained within the carton. The possibility of accidental opening of the tabs is greatly reduced if not eliminated. Further, as can be seen in the drawings above, the tabs are spaced from the outside corner of the carton, so as to overlie the anchor pins even when the anchor pins are fully inserted. Further the free ends of the tabs are located between the outside corner of the carton and the fold lines joining the tabs to the carton top wall. Thus, the tabs effectively shield a plastic liner within the carton from possible puncture or weakening due to contact with the anchor pins. If desired, an additional internal wall can be provided within the carton to close off the portion of the carton interior surrounding the tabs, although such has not been found to be necessary, due to the effective shielding offered by the tabs.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A protective barrier apparatus for protectively isolating a medical waste container having a top wall and a side wall joined together at an outside corner of the container, the apparatus comprising:
    a side panel for isolating the side wall of the container;
    a top panel joined to the side panel and extending at an angle therefrom, for isolating at least a portion of the top wall of the container;
    handle means joined to the top panel for lifting the apparatus into place on the container; and
    anchor means for releasably securing the apparatus to the container to prevent inadvertent dislodgment therefrom, said anchor means comprising portions of said handle means downwardly extending below said top panel.

2. The apparatus of claim 1 wherein said handle means comprises a generally U-shaped wire member.

3. An apparatus for the manual transport of articles by an operator which protectively isolates the operator from such articles, comprising:
    a paperboard container having a top wall and a side wall joined together at an outside corner of the container with a pair of tabs formed in the top wall having a free end remote from the side wall and a hinged end adjacent the side wall and connected to the top wall;
    a side panel of relatively impermeable material compared to the paperboard of said container for isolating the side wall of the container;
    a top panel of relatively impermeable material compared to the paperboard of said container, joined to the side panel and extending at an angle therefrom, for isolating the top wall of the container;
    handle means joined to one of the top and side panels for lifting the apparatus into place on the container; and
    anchor means carried on one of the top and side panels for releasably securing the apparatus to the container to prevent inadvertent dislodgment therefrom.

4. The apparatus of claim 3 wherein the top panel carries the anchor means and is smaller than the side panel.

5. The apparatus of claim 3 wherein the anchor means comprise pin means extending from the handle means, with the top panel interposed between the handle means and the pin means.

6. The apparatus of claim 3 wherein the side panel includes a peripheral border recessed below the side panel interior so as to extend toward the carton side panel.

7. A protective barrier apparatus for protectively isolating a container having a top wall and a side wall joined together at an outside corner of the container, the apparatus comprising:

a side panel for isolating the side wall of the container;

a top panel smaller than the side panel and joined to the side panel and extending at an angle therefrom, for isolating at least a portion of the top wall of the container;

handle means joined to the top panel for lifting the apparatus into place on the container; and anchor means carried on the top panel for releasably securing the apparatus to the container to prevent inadvertent dislodgement therefrom, said anchor means comprising pin means extending from the handle means, with the top panel interposed between the handle means and the pin means.

8. A protective barrier apparatus for protectively isolating a container having a top wall and a side wall joined together at an outside corner of the container, the apparatus comprising:

a side panel for isolating the side wall of the container;

a top panel smaller than the side panel and joined to the side panel and extending at an angle therefrom, for isolating at least a portion of the top wall of the container;

handle means joined to the top panel for lifting the apparatus into place on the container; and pin means carried on the top panel for releasably securing the apparatus to the container to prevent inadvertent dislodgment therefrom, with the top panel interposed between the handle means and the pin means.

9. An apparatus for the manual transport of articles by an operator which protectively isolates the operator from such articles, comprising:

a paperboard container having a top wall and a side wall joined together at an outside corner of the container;

a side panel of relatively impermeable material compared to the paperboard of said container for isolating the side wall of the container;

a top panel of relatively impermeable material compared to the paperboard of said container, joined to the side panel and extending at an angle therefrom, for isolating the top wall of the container;

handle means joined to one of the top and side panels for lifting the apparatus into place on the container; and anchor means carried on one of the top and side panels for releasably securing the apparatus to the container to prevent inadvertent dislodgment therefrom.

* * * * *